United States Patent [19]

Berndt

[11] Patent Number: 5,520,888
[45] Date of Patent: May 28, 1996

[54] BIO-MEDICAL WASTE REACTOR, STERILIZER AND METHODS THEREOF

[75] Inventor: Dieter R. Berndt, Incline Village, Nev.

[73] Assignee: Safe Alternatives Corporation, Ridgefield, Conn.

[21] Appl. No.: 189,669

[22] Filed: Feb. 1, 1994

[51] Int. Cl.$^6$ ........................................................ A61L 2/16
[52] U.S. Cl. ........................ 422/186.08; 472/28; 210/760; 588/205
[58] Field of Search .............................. 422/28, 186.08; 210/760; 588/205

[56] References Cited

U.S. PATENT DOCUMENTS

| | | | |
|---|---|---|---|
| 5,078,965 | 1/1992 | Pearson | 422/3 |
| 5,147,563 | 9/1992 | Long, Jr. et al. | 210/758 |
| 5,167,711 | 12/1992 | Wichner et al. | 106/705 |
| 5,190,725 | 3/1993 | Meijer et al. | 422/37 |

Primary Examiner—Donald P. Walsh
Assistant Examiner—Daniel Jenkins
Attorney, Agent, or Firm—Henry D. Coleman; R. Neil Sudol

[57] ABSTRACT

A reactor/sterilizer for disinfecting contaminated medical and/or biological waste comprises, in accordance with the present invention, at least one shredder/grinder to reduce in size solid waste to be disinfected, means to introduce waste into the shredder/grinder, a freezer or ice maker which traps disinfecting concentrations of ozone from an ozone generator in ice so that the ice can be added to the bio-medical waste prior to a shredding or grinding step. In a disinfecting method, the present invention relates to the treatment of biological and/or medical waste with ozone containing ice by admixing the ice with the the waste and allowing the ice to melt, thereby releasing ozone and exposing the waste to effective concentrations of ozone to disinfect the waste. In preferred embodiments, the instant biomedical reactor/sterilizer has both a coarse shredder/grinder and a fine shredder/grinder. The shredder/grinder produces a slush or slurry of waste and ice-containing ozone. As the temperature of the slurry increases, the entrapped ozone is released in a sustained manner as the ice melts over time and mixes with and disinfects the waste.

22 Claims, 1 Drawing Sheet

BIO-MEDICAL WASTE REACTOR, STERILIZER AND METHODS THEREOF

FIELD OF THE INVENTION

The present invention relates to methods for treating biological waste, including bio-medical waste utilizing treatments with ozone. The present invention also relates to reactor/sterilizer systems for carrying out sterilization methods according to the present invention and novel aspects of these systems.

BACKGROUND OF THE INVENTION

Ozone, the strongest of the common disinfecting agents, was used as early as 1893 for disinfection of drinking water in Holland. By 1916, there were 49 full-scale water treatment plants in Europe using ozone. Today, more than 2,000 water treatment plants throughout the world use ozonation for disinfection. Most of these plants are in Europe, with a particularly heavy concentration in France. Today, the principal uses of ozone are found in disinfecting water or in treating sewage.

In the United States, disinfection practice has principally relied upon the use of chlorine. However, because of concerns about byproduct formation during the disinfection process using chlorine, the alternative use of ozonation has generated considerable interest because of its ability to avoid the formation of halogenated organics. Still in an early developmental stage, the understanding of the actual mechanism of ozone reaction with biological material is not yet complete.

Ozone is characterized by strong oxidizing properties. It is an unstable gas at ambient temperatures and pressures and decomposes rapidly to oxygen at temperatures above 35° C. For this reason, it cannot be manufactured and packaged at a central manufacturing plant, but must be generated on site.

Ozone has a characteristic odor, which can be detected by humans at low concentrations (0.02 ppm by volume), far below the levels of acute toxicity. It is moderately soluble in water, with solubility dependent upon the temperature of the water and the concentration of the ozone in the feed gas. It is noted that although ozone has limited solubility in water, its solubility is about 10 fold greater than the solubility of oxygen in water (mole by mole comparison). Typically, low feed gas concentrations (about 1 to 8 percent by weight) are used in disinfection processes for treating water to assure virtual organism elimination (99.9% or greater) for most organisms.

As indicated above, ozone must be generated on site, and the gas stream, which generally contains about 1 to 8 percent ozone by weight, is applied to the water flow using appropriate gas/liquid contact conditions. Although ozone is highly reactive and will dissipate within a relatively brief time, ozone residual generally can be maintained for the period of time usually required for disinfection. In general, in water treatment disinfection processes, dissolved ozone residuals of approximately 0.4 to 0.5 mg/l have been typical objectives for the disinfection process lasting about 4 to 6 minutes. Using this ozonation process at a concentration of ozone of 0.4 ml/l achieves a 99.9% inactivation of Poliomyelitis viruses in 4 to 6 minutes.

In the United States, for water treatment purposes, ozone contact times ranging from about 4 to about 12 minutes are being considered. Criteria for future ozonation parameters in reactors/sterilizers will be affected by EPA CT criteria that will require consideration of hydraulic distribution characteristics within the individual reactor or configuration. These criteria are summarized in Appendix O of the U.S. EPA *Guidance Manual for Compliance with the Filtration and Disinfection Requirements for Public Water Systems Using Surface Water Sources.*

Ozone is thought to achieve disinfection largely through oxidation reactions that damage and destroy critical components of microorganisms. Ozone has been recognized as an effective disinfectant for a wide range of pathogens and is applicable for achieving the primary disinfection goals for the pathogen categories regulated in the EPA Surface Water Treatment Rule.

OBJECTS OF THE INVENTION

It is an object of the present invention to provide an improved bio-medical waste treatment system and method which will destroy bacterial and viral microorganisms, as well as other potentially hazardous organic by-products or constituents, in an environmentally friendly and acceptable manner.

It is an additional object of the present invention to provide a waste disinfection treatment process for treating infectious bio-medical waste via a continuous batch treatment process, utilizing a system of parallel joined fluid reaction vessels or tanks.

It is yet another object of the present invention to provide a bio-medical waste treatment system which has reaction vessels connected to a common fluid (liquid) feeder tank having an optional pressure injector or gas/liquid contactor to promote the efficiency of the system.

It is a further object of the present invention to provide a waste treatment apparatus for disinfecting infectious waste utilizing photo-excited ozone in a gas oxidation process to destroy bacterial and viral microorganisms.

It is still an additional object of the present invention to provide an apparatus utilizing mercury vapor radiation sources to optically excite ozone to a higher oxidative state which, in turn, creates additional ozone during contact with molecular oxygen while in aqueous solution.

It is yet a further object of the present invention to provide an apparatus which will more readily prepare infectious waste material for superior size reduction.

It is another object of the present invention to use frozen ozonated and photo-ozonated aqueous compositions to disinfect waste and separately, to provide both disinfection during a size-reduction stage as well as providing a means for cooling a mixture of bio-medical waste particles in contact with ozonated or photo-ozonated water within the reactor vessels.

It is a further object of the present invention to provide an apparatus and process for dewatering disinfected bio-medical waste to form a semi-solid sludge.

It is also an object of the present invention to provide an apparatus and process for encapsulating disinfected semi-solid sludge for further disposition and handling.

It is still a further object of the present invention to provide an apparatus and process for treating the effluent from a dewatering process and filtering such effluent for reuse in the overall disinfection system.

One or more of these and other objects of the present invention may be readily gleaned from the drawings and description of the invention which follows.

SUMMARY OF THE INVENTION

A reactor/sterilizer for disinfecting contaminated medical and/or biological waste comprises, in accordance with the present invention, at least one shredder/grinder to reduce in size solid waste to be disinfected, means to introduce waste into the shredder/grinder, a freezer or ice maker which traps disinfecting concentrations of ozone produced by an ozone generator in ice so that the ice can be added to the bio-medical waste to release ozone from the ice in a sustained release manner. Preferably, the ozone containing ice is added to the waste material prior to a shredding or grinding step.

In preferred embodiments, the instant bio-medical reactor/sterilizer has both a coarse shredder/grinder and a fine shredder/grinder. The fine shredder/grinder produces a slush or slurry from the waste and ice-containing ozone. In the slush/slurry containing finely ground bio-medical waste and ozone-containing ice, as the temperature of the slurry increases, the entrapped ozone is released in a sustained release manner as the ice melts over time and mixes with and disinfects the waste.

The reactor/sterilizer according to the present invention optionally contains a distributor designed to selectively and automatically distribute the waste which has been shredded along with the ozone-containing ice particles to at least one reactor tank where disinfection of the bio-medical waste occurs. In the reactor tanks aqueous solutions containing effective concentrations of ozone are added to disinfect the shredded waste. Preferably, more than one reactor tank is operatively connected in parallel to the distributor and each reactor tank is connected to a dewatering system which removes water to produce a semi-solid sludge which may be further encapsulated in plastics such as polyurethane foams and used as building materials or as fuel sources.

By operatively connecting the reactor tanks to the waste distributor in parallel, disinfection of the waste material may occur continuously. Following disinfection of waste in the reactor(s), the waste may then enter a dewatering system which removes water from the waste and produces a continuous flow of disinfected solid sludge or waste which can be prepared for incineration or packaged for land fill. The disinfected solid sludge material may also be encapsulated in polyurethane foams for use as building material or as a fuel source or frozen solid for transport.

The water which is removed from the disinfected bio-medical waste in the dewatering system may enter a liquids basin, from which the water may be specially treated and/or filtered for direct discharge into an existing sewage treatment facility or reused within the system.

The present invention also relates to methods for disinfecting bio-medical waste. In this method aspect, ozone-containing ice is introduced into a sample of bulk bio-medical waste material and the ice is allowed to melt. The melted ice releases ozone trapped within the ice into the bulk bio-medical waste in concentrations effective to eliminate a substantial population of microorganisms contaminating the bio-medical waste.

According to the present invention, a further method for disinfecting medical or biological waste comprises:

(a) introducing bulk bio-medical waste material into a shredding means;

(b) introducing into said shredding means along with said waste material ice containing ozone in concentrations effective for eliminating a substantial population of microorganisms contaminating said bio-medical waste after said ice melts and releases ozone;

(c) shredding said waste material and ice in said shredder to produce a slush comprising particles of waste material and ice, said particles varying in size to no greater than about ½ inch in diameter; and (d) allowing said ozone in said ice to disinfect the shredded bio-medical waste material.

In addition to the above-described method, the disinfecting method according to the present invention may utilize one or more further steps such as introducing the slush containing shredded waste material and ozone into a distributor to distribute the slush into more than one reactor. The disinfection reactors are preferably connected in parallel to allow the continuous disinfection of the waste material to take place.

In the present disinfection method, other optional steps which may be utilized in the present invention may include, for example, photoactivating the ozone to produce a photo-excited form of ozone which is incorporated into the ice for disinfection purposes and shredding the bio-medical waste in the presence of $CO_2$ or $N_2$ gas in order to facilitate the action of the photoexcited form of ozone to facilitate disinfection in the instant invention. Optionally, crushed ice containing ozone may be mixed prior to or after shredding the solid waste. The present invention may also include the step of injecting $N_2$ or $CO_2$ gas into the solid waste before a shredding/grinding step in order to brittelize soft materials in the waste material and render the shredding/grinding step more efficient. A further optional step according to the instant invention relates to a dewatering step which removes water from the disinfected sludge/slurry of medical waste and solidifies the disinfected waste for transport or packaging as building material or fuel.

In certain embodiments, ozone is first formed and dissolved in water in effective concentrations before the ozone-containing water is frozen into ice cubes or released as crushed ice or snow. Alternatively, ozone is produced directly in ice by photoexciting oxygen which is dissolved or trapped in the ice.

DETAILED DESCRIPTION OF THE INVENTION

Figure 1:
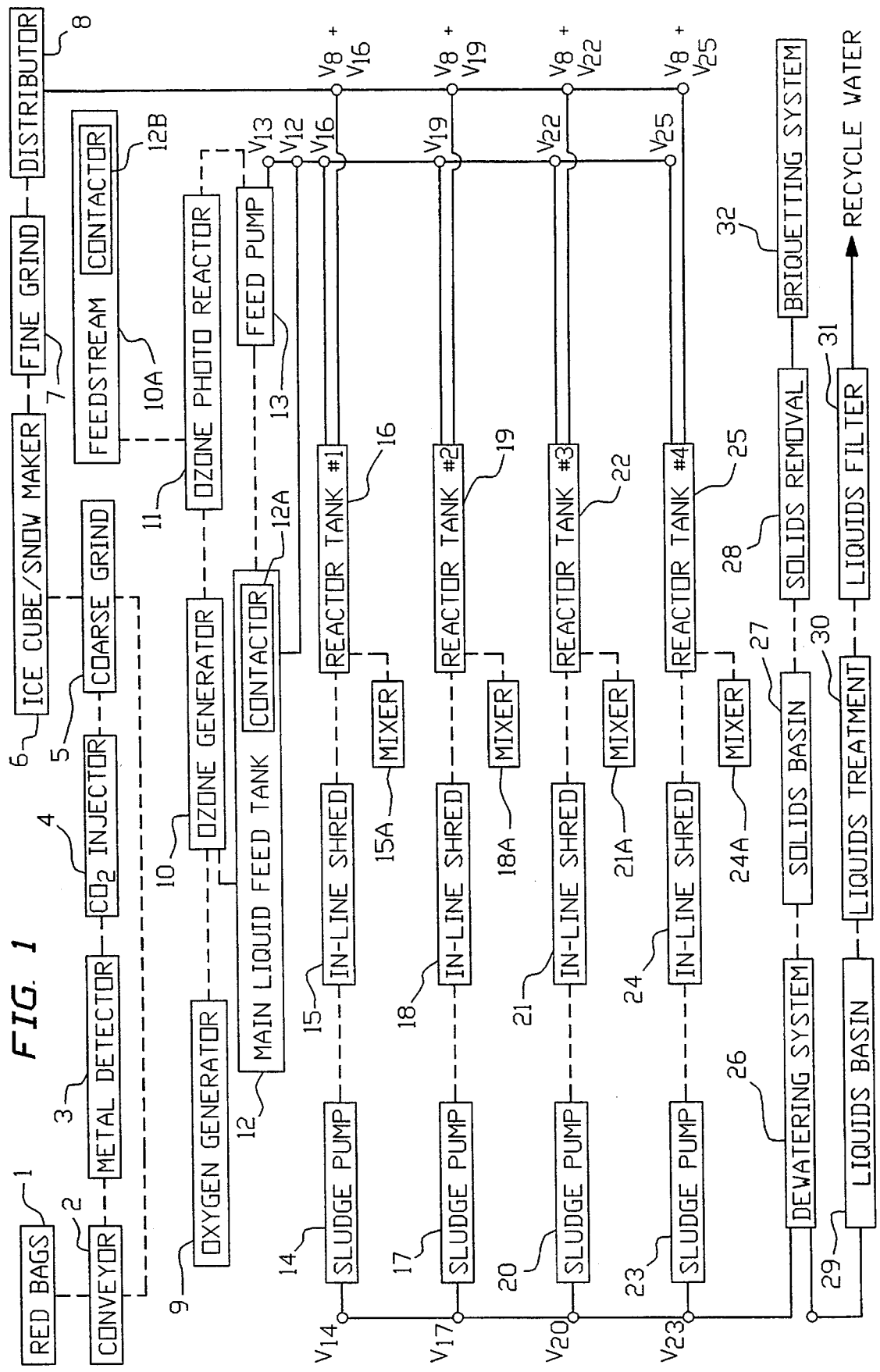
FIG. 1 is a flow diagram of the biomedical waste reactor of the present invention.

As used throughout the specification, the term "ozone" is used to describe the disinfecting agent used in the instant invention. Ozone is also known as triatomic oxygen or $O_3$·. Ozone has strong oxidizing properties and for this reason it is believed that ozone evidences such strong disinfectant properties as well. Ozone is typically produced using a commonly used corona discharge or ultraviolet generator acting upon the oxygen in the air (up to about 10% by weight or more of the solution) and is about ten times more soluble in water than is oxygen. It is both more stable and more soluble in aqueous solution as the temperature of the solution is reduced and is also more stable (i.e., has a much longer half-life) at a pH less than about 9.

It is to be understood that using lower concentrations of ozone will increase the contact time required to destroy a given number of bacterial and viral microorganisms and using high concentrations of ozone will decrease that time. Disinfection times according to the present invention may range from about 5 minutes up to one hour or longer, depending upon the degree of disinfection desired and the microorganisms present and their resistance to disinfection with ozone.

As used throughout the specification, the terms "effective", "effective amount" and "effective concentration" are used to describe concentrations or amounts of ozone which will effect a described objective such as eliminating a substantial population of microorganisms contaminating a bio-medical waste sample or, in certain instances, obtaining a complete microorganism kill (99.9+%) in a contaminated bio-medical waste sample.

In the present invention, an effective concentration of ozone may range, depending upon the final disinfection objective, from about 0.5 mg. to about 50 mg. or more per liter of aqueous solution. In the present invention, in preferred embodiments, in order to insure a 99.9+% kill rate for the common pathogens which occur in contaminated bio-medical waste, an initial ozone concentration of about 50 mg/L is preferably used along with the step of grinding the bio-medical waste to a particle size of less than about ½ inch in diameter. This concentration of ozone may be readily obtained by concentrating ozone in water at less than about 10° C. (preferably less than about 4° C. and most preferably at about 0° C.). At a temperature of less than about 10° C. the concentration of ozone and the half-life of ozone in solution may be increased. The effective disinfecting concentration of ozone for use in the present invention assumes a turbulent mixing of ozone in solution and a contacting time of at least about 15 minutes and preferably about 45 to about 60 minutes or more.

As used throughout the specification, the term "bio-medical waste" is used to describe a wide variety of biological and medical waste which is treated by the method of the instant invention. The bio-medical waste treated by the instant invention may included a wide variety of contaminated materials, including cotton sheets, pillow cases, bandages, cups, plates, diapers, scalpels, needles, syringes, pace-makers, catheters, human bones, skin tissue, human waste including urine and feces, urine and fecal stained gowns, plaster casts, glassware, laboratory vials and instruments, excess drugs and pharmaceuticals, rubber gloves, other bio-medical instruments which are made of plastic and non-metallic materials and other waste. Under most circumstances, the bio-medical waste is thoroughly contaminated with diseased human waste, blood, viruses, bacteria, molds and caustic chemicals. Other types of contaminated biological waste especially including human waste and animal waste in runoff may be treated by the method of the instant invention.

An exemplary disinfecting system utilizing the disinfecting method according to the present invention is illustrated in FIG. 1. As illustrated in FIG. 1, red bags or containers 1 containing contaminated bio-medical waste are loaded onto belt conveyor 2. The bags or containers are preferably colored (red) in order to indicate the containment of bio-medical hazardous waste. Red bags, which are generally used in the art to designate hazardous materials, are preferably made of biodegradable plastic material. Bio-medical waste is packaged and shipped in the red plastic bag containers.

Belt conveyer 2 delivers the off-loaded container 1 through a metal detector 3 and then up an incline to a coarse dry shredder 5. Exemplary conveying systems are readily available in the art and include, for example, those available from New London Engineering, New London, Wis., U.S.A. Metal detector 3 is preferably adjustable, similar to those used in airports, will be positioned preferably at a lower portion of the conveyor to screen the contents of container 1 for excessive metal content which may jam or impede the shredding/grinding process. In one preferred embodiment according to the present invention, if the metal detector is triggered, container 1 is off-loaded for manual inspection with a contamination-safe glove-box. Metal contents may be removed from container 1 before the container is placed back on belt conveyor 2.

Container 1 continues on belt conveyor 2 optionally through an injection station 4 in which an injection probe is automatically inserted into container 1. There, pressurized inert gas ($N_2$ or $CO_2$, but preferably $CO_2$) is forcibly injected into each container 1 in order to brittelize soft materials and prepare them for a more effective grinding and shearing. Solid bio-medical waste should undergo a thorough shredding or size reduction before it can be most effectively disinfected.

After the above-described injection step, container 1 continues up the conveyor to the coarse dry shredder 5 where the bio-medical waste is shredded to particles which are reduced in size to several inches or less in diameter. The coarse dry shredder 5 is preferably mounted above the tank vessels, is enclosed on 3 sides and is open at the conveyor end. Dry shredder 5 can shred solid waste and help in the safe destruction of bio-medical waste by reducing bulk volume up to 80% or more. The coarse dry shredder preferably incorporates a flail mill design used primarily to tear open bags and break up bundles of material and a rotor and impactor target plates which utilize a mixing action to break some of the material into smaller particles. Coarse dry shredders of this type are readily available in the art, from manufacturers such as Franklin Miller, Inc., Livingston, N.J., USA.

After being ground in the coarse dry shredder 5, the bio-medical waste is treated/mixed with ozonated ice cubes produced in an ice-cube maker 6, before being subjected to a fine grinding step. In certain embodiments, the addition of the ozonated ice cubes may occur prior to the coarse grinding/shredding step; preferably however, the ozonated ice cubes are added after the coarse grinding/shredding step and before a fine grinding/shredding step for enhanced efficiency of contacting the ozonated ice cubes with the waste.

In order to reduce the bio-medical waste to a much smaller size for efficient disinfection, the contents of the bio-medical waste from coarse shredder 5 are subjected to a further (fine) grinding/shredding step in fine shredder 7. A preferred design for the fine shredder incorporates a dual stage system. This system is available from Franklin Miller, Inc., Livingston, N.J., USA. In this system, the first stage operates with impactors and has one or more impactor target plates, as in the coarse ground shredder, performing a size reduction as waste is thrown onto the plates. In this first stage, as the waste material enters the machine, a rotor (usually having smaller teeth than in the coarse grinder) impacts the solid waste, breaking up some of the material into small particles. Preferably, the material is also "shot" toward the impactor plates where the waste undergoes yet another size reduction. In addition, a second stage includes a fixed-hammer mill designed as a shearing-type machine. This mill, which is essentially a series of knives or cutters bolted on the periphery of a disk, a number of which are stacked on a rotor shaft, provides the smallest particle sized for a given amount of power input. The shredder has a grate bar and/or screen which restricts the flow of shredded material to a certain size. Thus, utilizing the fine grinder/shredder according to the present invention, bio-medical waste may be fine ground to particles having diameters less than about ¼ inch. Fine shredder 7 reduces the bio-medical waste particles to sizes which are preferably less than about ½ inch in diameter and most preferably less than about ¼ inch.

As mentioned, the addition of ozonated ice cubes preferably occurs prior to the fine grinding/shredding step. In addition to providing a sustained release vehicle for releasing ozone during the grinding and sterilizing process, the ozonated ice cubes provide two additional functions. The first is to stabilize pathogens and begin a surface disinfection of the coarse ground bio-medical waste particles and the second is to establish a more effective shearing base for the bio-medical waste during the grinding/shredding step(s). While not being limited by way of theory, it is believed that the hard, brittle and, in certain cases, somewhat sharp ozonated ice cubes act to provide leverage in the fine grinding/shredding step(s).

Ice cube maker 6 produces ozone-containing ice used in the present invention. In this aspect, ozone is produced from oxygen and then is dissolved in water using any one of the commercially available ozone contactors (12A or 12B in FIG. 1). Ozone may be formed from atmospheric oxygen by corona discharge or in the presence of UV light as is readily known in the art. In the present invention, the production of ozone more readily occurs when the concentration of oxygen increases above that found in the earth's atmosphere (above about 21% by weight). To generate ozone in high concentrations, it is advantageous to produce the ozone from gas which contains at least about 90% by weight oxygen. Consequently, the inclusion of a commercially available oxygen generator 9 into the disinfection system facilitates the production of highly concentrated ozone for use in the present invention. Commercially available oxygen generating systems separate oxygen from air utilizing a unique Pressure Swing Adsorption (PSA) air separation process. The PSA process uses packed beds of molecular sieves (zeolite) which attract (adsorb) nitrogen from air at high pressure and release (desorb) it at low pressure before recycling. An exemplary oxygen generator for use in the present invention is available from AirSep Corp., Buffalo, N.Y., among others.

Oxygen produced by oxygen generator 9 is pumped into ozone generator 10 to produce ozone for use in the disinfection system. Although ozone may be generated by a number of energy sources, including ultraviolet radiation, electric corona discharge is the most common method employed in disinfection. Electric corona discharge (ozone) generators are available in a wide variety of configurations. Most of the ozone generators utilize a horizontal water-cooled tube configuration. Vertical tube and plate dielectric and air-cooled configurations are also available.

Ozone is formed in a corona discharge by the interaction between an electric discharge and oxygen molecules in a gas stream that is passed through the generator. The electric discharge is induced by an alternating current which creates a voltage cycle across a gap between two electrodes. One of the electrodes is coated with glass or ceramic dielectric material that provides a smooth surface to distribute the electric discharge that can produce an undesirable and wasteful arcing at voltages below the level at which ozone can form. Ozone generators employing these design features are well known in the art. In the present invention, medium and high frequency generators are used to produce ozone. As is known in the art, increased frequency generators can generally produce higher concentrations of ozone within the gas stream.

While there are no hard rules for selecting ozone generator types for use in the present invention, one of ordinary skill in the art will recognize that the frequency of the generator, voltage, capability for turndown, required concentration of ozone in the gas stream, the generator cooling requirement, the size of the generator as well as the gas-to-liquid ratio in contacting systems as well as the type of ozone contactor used will influence the generator chosen for use in the instant system. The ozone generator should include means for measuring the concentration of ozone in the gas phase in order to establish and maintain consistent disinfecting concentrations of ozone.

Optionally, the ozone generated in ozone generator 10 may be fed into ozone photo reactor 11. The use of ultraviolet radiation converts free ozone and/or hydrogen peroxide into hydroxyl radicals. This reaction permits the formation of hydroxyl radicals which will produce effective oxidation of numerous organic compounds in the bio-medical waste which may resist ozone by itself. Hydroxyl radicals also decontaminate the effluent water and purifies it for eventual re-use in the ozone contacting/disinfection process. This allows the water from the bio-medical waste reactor to remain in a closed-loop cycle, thus eliminating concerns about effluent water discharge.

Ozone produced by ozone generator 10 may be delivered into a feed stream 10A, preferably chilled to about 0–° C., through ozone contactor 12B. The contactor is used to maximize the contact of the ozone with the solution in order to enhance the concentration of ozone. A number of ozone contactor types may be used in the present invention. In general, ozone is is drawn into the process flow stream through an aspirator, which operates by a venturi-jet. Exemplary contactors include the Otto contactor device and in-line static devices, among others. These may be purchased from a number of suppliers including Aqua-Flo Inc., Baltimore, Md. USA. The concentration of ozone in feed stream 10A may be monitored by means of gas phase monitors in the ozone supply stream and in the off-gas stream. Excessive or insufficient ozone concentration in the off-gas may be a general indicator of an excessive or insufficient ozone dose.

Feed stream 10A, which contains high concentrations of ozone preferably in a chilled state, then introduces ozone into ice cube maker 6. Ice cube maker 6 is an industrial automatic ice cubing system which has the capacity to freeze the ozone containing solution from feed stream 10A in a short period of time (generally, less than about 30 minutes and preferably less than about 15 minutes). Such a system may be available from Semco Manufacturing Co., Pharr, Tex., USA. In addition, as explained hereinbelow, feed stream 10A may be super-cooled to −20° C. before freezing in order to obtain high concentrations of ozone. As an alternative to ice cube maker 6, an industrial snow/slush maker (available from Vivian Corp., St. Louis, Mo., among others) may be utilized to produce an ozone sample entrapped in small particles of ice. The ozone containing snow/slush may be added at any step of the disinfection process.

The ozone-containing ice/snow produced in ice cube maker 6 may be readily mixed with the bio-medical waste at any time before or during the actual step of disinfection in a reactor tank. Preferably, however, the ice is mixed with the shredder after the coarse grinding/shredding step and before a fine grinding/shredding step. In embodiments which utilize snow/slush instead of ice, the snow/slush may be added to the waste at any time during the disinfection process without the need to grind or shred.

During the fine grinding/shredding step, the size-reduced bio-medical waste particles and ice forms a frozen slush-like composition which flows by gravity or conveyor (e.g. standard or screw conveyor) into distributor 8. In preferred embodiments according to the invention, distributor 8 is designed to selectively and automatically distribute the frozen bio-medical waste slush to reactor tanks 16, 19, 22 and 25, which are connected in parallel.

Disinfection of the shredded bio-medical waste occurs in the reactor tanks. Because of the corrosive, oxidative nature of ozone, the tank material should be chosen from amongst stainless steel, glass, ceramics or polyethylene. For simplicity and cost efficiency, the reactor tank is optimally made of ½ inch thick polyethylene- similar to tanks which are already approved as long-term septic sewage tanks. Above ground tanks, such as those manufactured by Hancor Equipment, Findlay, Ohio, may be used for the disinfection, ozonation, contacting and hydroxyl reaction processes.

The reactor tanks may be used alone or may optimally connected in parallel. By having reactor tanks 16, 19, 22 and 25 connected in parallel, an efficient and continuous disinfection/cycling of bio-medical waste in the reactor tanks is possible. In at least one embodiment according to the invention, reactor tanks 16, 19, 22 and 25 are connected such that each tank is capable of receiving up to 4,000 pounds of solid bio-medical waste within a certain time-cycle in order to facilitate the continuous cycling of the bio-medical waste and the complete disinfection of the bio-medical waste. The parallel design in this aspect of the instant invention advantageously provides a means to allow maintenance of one or more of the reactor tanks while disinfection occurs. Thus, by using more than one reactor tank which is connected in parallel no disinfection down-time will result during maintenance of any one reactor tank. In a preferred embodiment, at least one of the reactor tanks 16, 19, 22 or 25 provides a continuous back-up to the system at all times. By disinfecting bio-medical waste in discrete reactor tank units, a greater quality control for the system will also result.

After bio-medical waste is delivered into reactor tank 16, an aqueous solution of ozone gas is pumped into reactor tank 16. The amount of bio-medical waste delivered into tank 16, ranges, but is generally about 4,000 pounds and the amount of water solution is typically about 2,000 gallons. Tank 16 has a mixer 15A and/or a homogenizer for mixing and/or homogenizing the waste as it is being disinfected. By way of example, in FIG. 1, Tank 16 is fitted with its own sludge pump 14 and in-line shredder 15 which thoroughly mix and mechanically homogenize the disinfecting gas and bio-medical waste particles such that optimal disinfection occurs. Sludge pumps 14, 17, 20 and 23 are preferably automatic self-priming and capable of handling solids of appropriate size. Sludge pumps 14, 17, 20 and 23 are also capable of pumping disinfected bio-medical waste to dewatering system 26. A recommended sludge pump is manufactured by Godwin Pumps of America, Inc., Bridgeport, N.J. Tanks 16, 19, 22 and 25 may also be fitted with commercial mixers 15A, 18A, 21A and 24A such as a spiral jet mixer available from Flo Trend Systems, Inc., Houston, Tex., USA, to facilitate the mixing action of the sludge in the tank(s) during disinfection.

The disinfection time in a reactor tank may vary over a wide range, but in preferred embodiments according to the present invention, a disinfection period of about 45 minutes to about one hour has been shown to be effective and is preferred. Periods of disinfection outside of this range will depend upon the batch size to be disinfected, the size of the particles and the amount of ozone containing ice previously added to the mixture, among other factors.

In a preferred method, the disinfection process is allowed to continue for a period of up to 60 minutes. In the present invention, the disinfection process utilizes ozone produced by coronal discharge, among other methods well-known in the industry. The present invention, in certain embodiments, also makes use of photo reactive ozone. It has unexpectedly been discovered in the instant invention that the use of photo reactive ozone may be advantageously employed because of its longer duration of action. Thus, in certain preferred embodiments according to the instant invention, photo reactive ozone is continually being generated from ozone. By way of example, ozone is produced in ozone generator 10 and subsequently excited in photo reactor 11 to produce photoreactive ozone. "The photo reactive ozone then may be pumped into the main liquid feed tank 12 by feed pump 13, or alternatively, ozone may be pumped directly into solution in feed tank 12 through ozone contactor 12A. Ozone may also be directly pumped into the individual reactor tanks. Optimally, main feed tank 12 always has at least about 4000 gallons of water with an effective average gas to liquid concentration which ranges from about 5 mg to more than 100 mg per liter, with an optimum of about 50–100 mg of ozone per liter of water.

Generally, in preferred embodiments according to the present invention, about 2,000 gallons of water containing ozone at a concentration of about 50 mg. per liter of water are initially discharged into reactor tank 16 approximately every 60 minutes. The concentrations of ozone chosen for the disinfection step may vary depending upon the bio-medical waste sample and organism to be disinfected. It is noted that certain anaerobic bacteria and viruses may require relatively high concentrations of ozone (ie., greater than about 5 mg./L and in certain cases as high as about 25 mg./L) to effect 99.9+% disinfection of contaminated waste material. Further concentrations of ozone may be added to the reactor tank in order to maintain the optimal concentration of ozone therein at about 50 mg/L for a period of about 60 minutes, in order to assure disinfection. Thus, ozone is produced at a concentration level in solution in main feed tank 12 which is effective to provide a relatively stable and homogeneous concentration of ozone in solution in any reactor tank (16, 19, 22 or 25) of about 50 mg./L for a period of at least 15 minutes and preferably about 60 minutes or longer. The use of this methodology thus ensures the continuity of disinfecting liquid for each of the reactor tanks that can be maintained within the optimum concentration range of ozone for periods of time sufficient to disinfect the bio-medical waste. In addition, each reactor tank 16, 19, 22 or 25 is preferably sealed in order to minimize escaping gas and thus allow the concentration of ozone in solution to equilibrate. Sealing the reactor tank and equilibrating ozone in solution during disinfection will limit and possibly eliminate the need to continually add ozone during the disinfection period to maintain an effective disinfecting concentration of ozone in solution in the reactor tank.

Reactor tanks 16, 19, 22 and 25 are preferably connected in parallel. By way of example, 4,000 pounds of shredded medical waste slush are delivered into reactor tank 16 from distributor 8. Soon thereafter, about 2,000 gallons of water containing a disinfecting concentration of ozone are pumped into reactor tank 16 and allowed to disinfect the bio-medical waste for a period of at least about 15 minutes and preferably about 45 to about 60 minutes. During the disinfecting period in reactor tank 16, reactor tank 19 is being filled with 4,000 pounds of newly shredded bio-medical waste. The same disinfecting process in reactor tank 19 follows about 45–60 minutes behind the process described above for reactor tank 16. Likewise, the same disinfecting process in reactor tank 22 follows about 45–60 minutes behind the process described above for reactor tanks 16 and 19. In this manner, shredded bio-medical waste is cycled through the system with at least one reactor tank effecting disinfection at any given time. As exemplified by reactor tank 25, in the described embodiment, a back-up tank serves to maintain system continuity should a malfunction occur or maintenance of one or more of the other reactor tanks be required.

After a period of disinfection, the contents of reactor tank 16, 19, 22 or 25 are discharged to dewatering system 26 via sludge pumps 14, 17, 20 or 23. This discharging process takes a period of time ranging from less than about 15 minutes to about one hour or more, and in a continuous system, about 45 minutes to an hour, after which time the discharged reactor tank is available to begin the disinfection cycle once again.

Thus, in an embodiment of the present invention, while the discharging process in reactor tank 16 is occurring, reactor tank 19 has been loaded with waste and the disinfection cycle has commenced and reactor tank 22 is being filled with newly shredded bio-medical waste. Thus, in at least one embodiment, the present system makes use of multiple disinfection tanks connected in parallel to maximize the amount of bio-medical waste which can be disinfected in a given time period by the system.

Dewatering of the disinfected bio-medical waste from reactor tank 16, 19, 22 or 25 occurs in a dewatering system 26. The dewatering system may comprise any system which is capable of removing water from the disinfected bio-medical waste, but the system of choice utilizes a transition screen separator. In this transition screen separator dewatering system, the disinfected sludge/slurry of bio-medical waste moves across at least one inclined screen such that the screen surface(s) produces a rapid separation of solid material from water. During the dewatering process, the water contained in the bio-medical sludge/slurry runs off into a liquids basin 29.

After the sludge/slurry of waste has been sufficiently dewatered, the sludge is discharged to a solids basin 27. In the solids basin 27, the sludge material can be prepared for incineration or packaged for use in land fill applications. An optional briquetting system 32 may be outfitted from solids basin 27. Briquetting system 32 (available from Gensco) may comprise a compacting system which makes a variety of geometric shapes,, such as logs or bricks in order to make the compacted and decontaminated medical waste easy to transport, dispose or encapsulated with polyurethane foams for use as building material. An exemplary briquetting system is available from Flo Trend Systems, Inc., Houston, Tex. The sludge material may also be frozen into solid ice cube blocks for ease of transport.

Liquids basin 29 fills up with effluent residual water from the dewatering stage of the process. In general, the amount of water which runs off into the liquids basin from the treated sludge/slurry varies according to the amount of ozonated ice/slush and ozone containing disinfection solution added to the bio-medical waste. In the system described herein, the amount of water which runs off into liquids basin 29 generally ranges from less than 1000 gallons to over 2,000 gallons per hour, usually about 1500 gallons per hour. The liquid discharge in liquids basin 29 is then specially treated in liquids treatment or hydroxyl reactor 30 (with hydroxyl radicals generated in ozone photo reactor 11) or filtered in liquids filter 31 with an activated filter material such as charcoal in a separate filter tank for reuse in the disinfection system or alternatively, for direct discharge into an existing sewage treatment facility. Exemplary dewatering and filtering systems are available from Flo Trend Systems, Inc., Houston, Tex.

The following examples are provided to illustrate the present invention and should not be construed to limit the scope of the invention of the present application in any way.

EXAMPLE 1

IN VITRO EXPERIMENTAL DISINFECTION STUDIES

Direct activity of ozone (trioxygen) is assessed in vitro using cells, protozoa, bacteria, fungi and viruses commonly found in medical waste. Unless otherwise indicated, the ozone is dissolved in water to give an average concentration of about 50 mg/L as a working concentration and is further diluted in culture in which a particular organism is grown. Solvent (water) alone and reference strains are used as controls.

Direct biological activity of ozone is tested on microorganisms which are common to the infectious biological waste material discarded as red-bag medical waste by hospitals and clinics; the activity is assessed on the basis of minimum inhibition concentration (MIC) as well as minimum pathogen concentration (MPC) after standard overnight incubation in culture.

Results are summarized in Table 1, below. From the table, it is evident that certain standard microorganisms that have been identified as resistant to conventional disinfectants exhibit uniform sensitivity to ozone in the same manner as are the sensitive organisms. Those isolates with known sensitivity to most disinfectants, including ozone, include International Strains: *Pseudomonas aureus* (ATCC 26923), *Pseudomonas aeruginosa* (ATCC 27853) and *Escherichia coli* (ATCC 25922).

The solvent or culture medium without ozone does not inhibit the in vitro growth of bacteria, fungi, protozoa and viruses in the studies. Results of the studies are as follows:

A. Effect of Ozone on *Leshmania donovani* promatigotes IN VITRO

Ozone is dissolved in water at a concentration level of 50 mg/L is added to the culture medium to a final ozone concentration level of 15 mg/L. The diluted culture medium evidences the killing of all promatigotes (99.9+%) within 20 minutes.

B. Effect of Ozone on Myeloma Cell Line and Spermatozoa

Utilizing the final ozone concentration of 15 mg./L human spermatozoa are destroyed (99.9+%) within a period of about 5 minutes and the myeloma cells are destroyed (99.9+%) within a period of about 45 minutes.

C. Effect of Ozone on Microorganisms

All microorganism disinfection is based on the 15 mg/L ozone concentration levels in water; the activity is assessed on the basis of minimum inhibition concentration (MIC) as well as the minimum pathogen concentration (MPC).

1. Diarrhoeal Diseases (i) Salmonella sp.

(ii) Shigella sp.

(iii) Enteropathogenic/enterotoxigenic *Escherichia coli*

2. Urinary Tract Infections: Bacterial and Fungal (i) *Neisseria gonorrhoea* (PPNG and non-PPNG)

(ii) *Candida albicans*

(iii) Pseudomonas Sp.

3. Bacteria Causing Respiratory Tract Infections (i) Klebsiella sp.

(ii) *Staphylococcus aureus*

(iii) *Staphylococcus epidermidis*

4. Other Infections Caused by Bacteria (i) Proteus (ii) Achromobacter (iii) *E. coli*

5. Fungal Infections (i) Common dematophytes
   a) *Trichophyton violaceum*
   b) *Trichophyton canis*

(ii) Systemic Fungi
   a) Cryptococcus sp.
   b) Candida sp.

(iii) Other General Fungi
   a) *Phialophora verrucose*
   b) Penicillium Sp.

6. Viral Diseases (i) Human Immunodeficiency Virus (HIV)

(ii) Hepatitis A/B (iii) Epstein Barr (iv) Herpes (v) Meningitis

TABLE 1

MIC and MPC of Ozone On Various Pathogens in Agar

| PATHOGEN | N. | MIC (mg/ml) | MPC (mg/ml) |
|---|---|---|---|
| Gram Positive Cocci | | | |
| S. aureus | 16 | 0.015 | 1.25 |
| S. epidermidis | 14 | 0.015 | 1.25 |
| S. aereus | 1 | 0.015 | 1.25 |
| Gram negative cocci | | | |
| N. gonorrhoea | 49 | .015 | 1.25 |
| Gram negative bacilli | | | |
| Salmonella | 3 | .008 | 1.25 |
| Shigella | 7 | .005 | 1.25 |
| EPEC/ETEC | 16 | .015 | 1.25 |
| Pseudomonas | 1 | .015 | 1.25 |
| P. aeruginosa | 1 | .015 | 1.25 |
| Klebsiella | 1 | .008 | 1.25 |
| E. coli | 1 | .005 | 1.25 |
| Achromobacter | 1 | .005 | 1.25 |
| Fungi | | | |
| C. albicans | 5 | .015 | 1.25 |
| Triviolaceium | 1 | .006 | 1.25 |
| Tricanis | 1 | .006 | 1.25 |
| Cryptococcus | 1 | .006 | 1.25 |
| Ph. verrucose | 1 | .006 | 1.25 |
| Penicillium | 1 | .006 | 1.25 |
| Virus | | | |
| HIV | 34 | .005 | 1.25 |
| Hepatitis A | 25 | .015 | 1.25 |
| Hepatitis B | 15 | .015 | 1.25 |
| Epstein Barr | 30 | .015 | 1.25 |
| Herpes | 15 | .015 | 1.25 |
| Meningitis | 15 | .015 | 1.25 |

N = Number of isolates; MIC = Minimum Inhibition Concentration; MPC = Minimum Pathogen Concentration; EPEC/EPTEC = enteropathogenic *Escherichia coli*/enterotoxigenic *Escherichia coli*.

Results

Minimum inhibition concentrations (MIC) as well as minimum pathogen oncentrations (MPC) of soluble ozone on the above-described pathogens is determined. Standard disinfection materials and in certain cases, reference strains, are used as controls and for comparative purposes. The results are summarized in Table 1, above.

The results indicate that soluble ozone will produce an in vitro kill rate of approximately 100% of microorganisms which infect bio-medical waste at an average concentration of ozone of no greater than about 0.015 mg/ml or about 15 g/L. Based upon the results presented herein and the half-life associated with ozone in solution, it is expected that concentrations of ozone of about 50 mg/L for use in the present invention will produce completely effective disinfection of bio-medical waste treated by the present method.

EXAMPLE 2

OZONATED ICE PROCESS

The development of long half-life ozone is accomplished by injecting ozone along with oxygen carrier gas to produce a gas to liquid concentration level of at least about 50 mg. of ozone per liter of water. By way of example, the ozone which is produced is injected into refrigerated water which is held in an insulated holding tank which has been filled with refrigerated water. Into the water in the holding tank is connected a venturi-jet high pressure contactor which thoroughly mixes ozone in the water. When a concentration level of 50 mg/L of ozone in solution is reached, the ozonated water is recycled through a refrigeration unit providing a super-cooling effect down to a temperature below about $-20°$ C. At this temperature of the solution, quite unexpectedly, the ozone gas begins to liquify within the super-cooled water, hence making it miscible in the water. This liquification process takes only about five or ten minutes to complete. The super-cooled ozonated water is then injected directly into the disinfection reactor which contains the shredded medical waste. Alternatively, the super-cooled ozonated water may be utilized directly in a snow/ice blower as previously described which makes ozonated ice crystals for decontaminating the medical waste during the grinding/shredding process.

Ozone concentration levels and super-cooling temperatures can be adjusted to fine-tune the process for the generation of ozonated snow/ice for numerous other waste treatment and disinfection systems.

Biological and/or medical waste is treated with the above-described ozone containing ice by admixing the ice with the the waste and allowing the ice to melt, thereby releasing ozone and exposing the waste to effective concentrations to disinfect the waste.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

I claim:

1. A method of disinfecting medical or biological waste comprising:

(a) introducing bulk bio-medical waste material into a shredder;

(b) introducing, into said shredding means along with said waste material, ice containing ozone in concentrations effective to produce aqueous ozone in a concentration of about 0.5 mg/liter to about 50 mg/liter after said ice melts;

(c) shredding said waste material and ice in said shredder to produce a slush comprising particles of waste material and ice, said particles varying in size to no greater than about ½ inch in diameter; and (d) allowing said ice to melt so as to expose said shredded bio-medical waste material to ozone released from said ice.

2. The method according to claim 1 further comprising the step of dewatering the disinfected bio-medical waste from step (d) to produce solid waste material.

3. The method according to claim 2 further comprising the steps of introducing said slush containing shredded waste material and ozone into a distributor; distributing said slush from said distributor into at least one disinfection reactor; and disinfecting said bio-medical waste in said reactor.

4. The method according to claim 3 wherein said slush is distributed into at least two disinfection reactors connected in parallel.

5. The method according to claim 4 wherein said step of disinfecting said bio-medical waste occurs continuously.

6. The method according to claim 1 wherein said ozone is photoactivated ozone.

7. The method according to claim 1 further including the step of shredding said bio-medical waste in the presence of $CO_2$ or $N_2$ gas.

8. A method of disinfecting medical or biological waste comprising:

(a) introducing bulk bio-medical waste material into a shredding means and shredding said waste into particles which vary in size to no greater than about ½ inch in diameter;

(b) introducing into said shredded waste ice containing ozone in concentrations effective to produce aqueous ozone in a concentration of about 0.5 mg/liter to about 50 mg/liter after said ice melts; and (c) allowing said ice to melt so as to expose said shredded bio-medical waste material to ozone released from said ice.

9. The method according to claim 8 including the step of further shredding said shredded waste in combination with said ice.

10. The method according to claim 8 further comprising the step of dewatering the disinfected bio-medical waste from step (c) to produce solid waste material.

11. The method according to claim 9 further comprising the step of introducing said shredded waste material and said shredded ice into a distributor before distributing said waste material and ice into at least one disinfection reactor and disinfecting said bio-medical waste.

12. The method according to claim 11 wherein said shredded waste material and shredded ice are distributed into at least two disinfection reactors connected in parallel.

13. The method according to claim 12 wherein said step of disinfecting said bio-medical waste occurs continuously.

14. The method according to claim 11 wherein said disinfecting step includes the step of exposing said shredded waste to an aqueous solution containing a concentration of ozone effective to eliminate a substantial population of microorganisms contaminating said bio-medical waste.

15. The method according to claim 8 wherein said ozone is photoactivated ozone.

16. The method according to claim 8 further including the step of shredding said bio-medical waste in the presence of $CO_2$ or $N_2$ gas.

17. A disinfection system for disinfecting bio-medical waste comprising:

(1) at least one shredder for shredding bulk bio-medical waste into particles;

(2) an ozone generator;

(3) an ice maker in communication with said shredder;

(4) an ozone contactor operatively connected to said ozone generator, said contactor releasing effective concentrations of ozone into an aqueous solution in a feed stream to produce an ozone-containing solution, said feed stream releasing said ozone-containing solution into said ice maker, said ice maker producing ozone-containing ice from said ozone-containing solution and releasing said ice into said bio-medical waste particles; and (5) at least one ozone reactor in communication with said shredder, said shredder delivering said bio-medical waste and said ozone-containing ice into said reactor.

18. The disinfection system according to claim 17 having a distributor in communication with said shredder and said reactor for distributing said particles of shredded bio-medical waste from said shredder to said reactor.

19. The disinfection system according to claim 18 containing at least two reactors, said reactors communicating with said distributor in parallel.

20. The disinfection system according to claim 17 wherein said shredder reduces the size of said bio-medical waste particles to less than about ½ inch in diameter.

21. The disinfection system according to claim 17 having at least two shredders, at least one of said shredders shredding said bio-medical waste and said ozone containing ice into particles of less than about ½ inch in diameter.

22. A method of disinfecting biological or medical waste comprising mixing bulk biological or medical waste and ice containing ozone and allowing said ice to melt so as to expose said waste to ozone released from said ice.

* * * * *